United States Patent [19]
Wada

[11] Patent Number: 5,253,650
[45] Date of Patent: Oct. 19, 1993

[54] APPARATUS FOR RECORDING AN ELECTROCARDIOGRAM

[75] Inventor: Yoshihiro Wada, Nara, Japan

[73] Assignee: Sharp Kabushiki Kaisha, Osaka, Japan

[21] Appl. No.: 677,544

[22] Filed: Mar. 29, 1991

Related U.S. Application Data

[63] Continuation-in-part of Ser. No. 521,705, May 10, 1990, abandoned.

[30] Foreign Application Priority Data

May 16, 1989 [JP] Japan ................................ 1-123563

[51] Int. Cl.⁵ ............................................ A61B 5/044
[52] U.S. Cl. ................................................... 128/712
[58] Field of Search ............... 128/696, 706, 710, 712

[56] References Cited

U.S. PATENT DOCUMENTS

| | | | |
|---|---|---|---|
| 3,267,933 | 8/1966 | Mills et al. | 128/712 |
| 3,561,428 | 2/1971 | Jacobson | 128/712 |
| 3,587,564 | 6/1971 | Hagan et al. | 128/712 |
| 3,793,626 | 2/1974 | Zambuto | 128/710 |
| 3,874,370 | 4/1975 | Harris et al. | 128/712 |
| 4,068,310 | 1/1978 | Friauf | 128/710 |
| 4,187,858 | 2/1980 | Day et al. | 128/712 |
| 4,223,683 | 9/1980 | Lown et al. | 128/706 |
| 4,420,000 | 12/1983 | Bailey | 128/706 |
| 4,606,352 | 8/1986 | Geddes et al. | 128/712 |

Primary Examiner—William E. Kamm
Attorney, Agent, or Firm—David G. Conlin; Robert F. O'Connell

[57] ABSTRACT

The apparatus for recording an electrocardiogram capable of displaying a change of spike intervals of adjacent QRS groups among a plurality of QRS groups of an electrocardiographic wave, the apparatus capable of displaying a time change of an electric potential with heart pulsations, the QRS groups showing an electric potential at a start of a ventricular systole includes a first memory unit for storing a measured electrocardiographic wave proportional to a predetermined time period, a unit for detecting a reference point of each R wave of the QRS groups in the electrocardiographic wave stored in the memory unit, a unit for displaying the electrocardiographic wave stored in the memory unit, and a control unit for controlling the display unit so that a reference point of one of the QRS groups in the electrocardiographic wave is displayed at a predetermined position on displaying unit, the control unit being capable of shifting the QRS groups in a time scale while the electrocardiographic wave is displayed on the display unit.

11 Claims, 10 Drawing Sheets

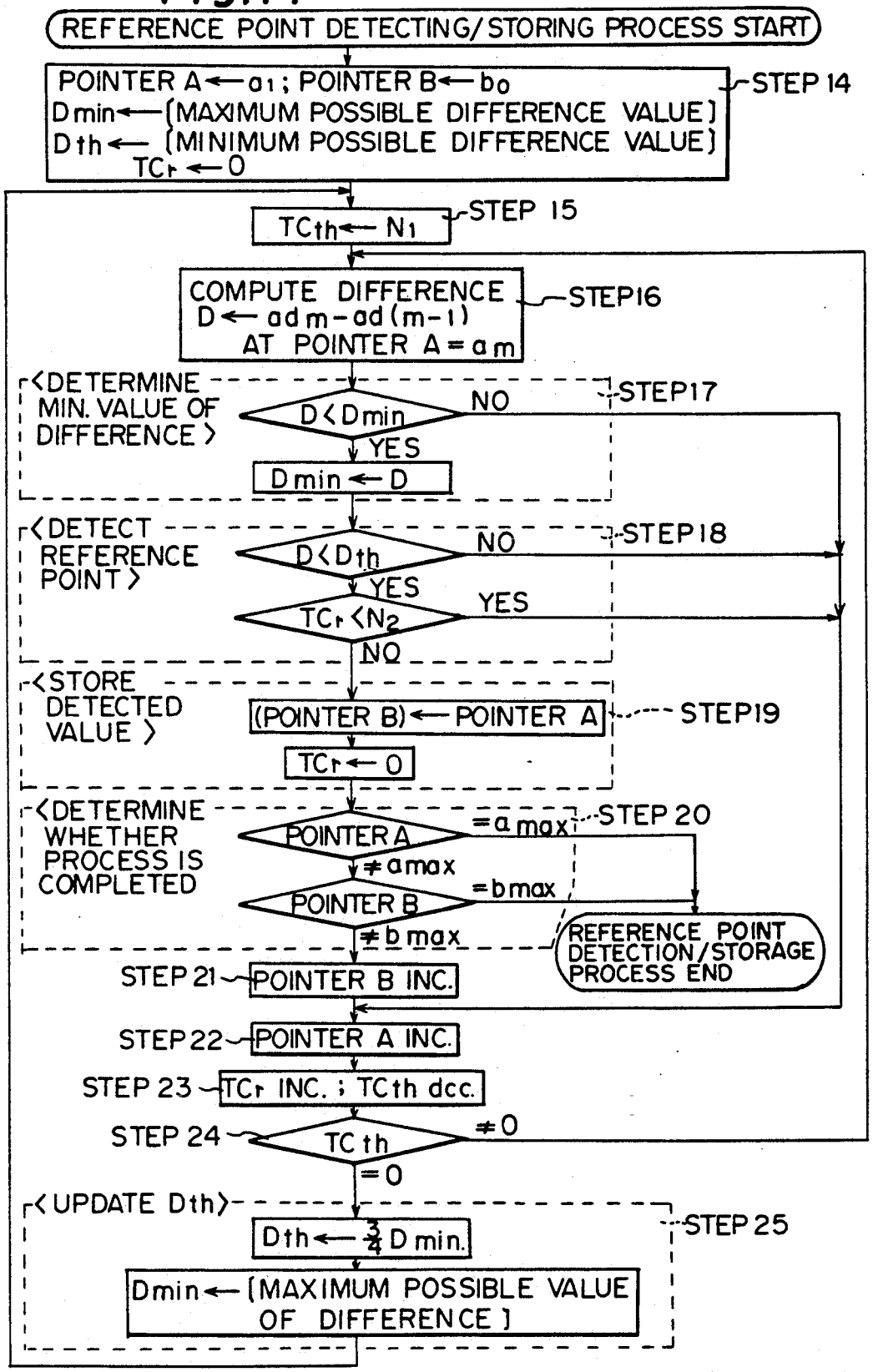

APPARATUS FOR RECORDING AN ELECTROCARDIOGRAM

CROSS-REFERENCE TO RELATED APPLICATION

This application is continuation-in-part application of U.S. Ser. No. 521,705 filed on May 10, 1990, now abandoned.

BACKGROUND OF THE INVENTION

1. Field of the Invention

The present invention relates to a portable recording apparatus for an electrocardiogram. More particularly it relates to a recording apparatus of electrocardiographic waves which has a display unit such as a liquid crystal display device for displaying recorded electrocardiographic waves such as Holter electrocardiograph.

2. Description of the Related Art

The inventors of the present application know an electrocardiogram recording apparatus capable of confirming the recording status and making diagnoses easily as irregular pulses by displaying the recorded electrocardiographic waves on a display device composed of liquid crystal.

In this apparatus, the electrocardiographic wave is sequentially displayed as a static waveform from left to right on the display screen. Once the wave reaches the right end of the display screen, a new wave is sequentially displayed by erasing the previous waveform, which has just been displayed. This method of displaying the waveform has been commonly used for monitoring the electrocardiogram.

Such a known apparatus as described above has disadvantages. For example, when three QRS groups (spikes corresponding to the start of a ventricular systole), indicating the time change of an electric potential with heart pulsations, are displayed from left to right on the display screen in order, the display position of the QRS group displayed on the leftmost end of the screen is not fixed, but is changed by displaying a new waveform thereon. As a result, it is difficult to visualize intervals between the R wave in a QRS group and the R wave in the next QRS group to be displayed to the right of the already generated QRS group, that is, it is difficult to visualize a change of R-R intervals (the change of a heart-beat rate). Furthermore it is difficult to capture the R-R interval between the R wave in the QRS group on the rightmost end of the display screen and the R wave in the next QRS group to be displayed on the leftmost end of the screen, since the display between the R-R interval will be interrupted.

SUMMARY OF THE INVENTION

It is an object of the present invention to provide an electrocardiogram recording apparatus capable of visualizing the changes of the R-R intervals easily, particularly at an adjacent R-R interval among a plurality of spikes or QRSs of the electrocardiographic wave which indicates the time change of an electric potential with heart pulsations corresponding to the start of a ventricular systole.

The object of the present invention can be achieved by an apparatus for recording an electrocardiogram capable of displaying a change of spike intervals of adjacent QRS groups among a plurality of QRS groups of an electrocardiographic wave, the apparatus capable of displaying a time change of an electric potential with heart pulsations, the QRS groups showing an electric potential at a start of a ventricular systole, the apparatus includes a first memory unit for storing a measured electrocardiographic wave proportional to a predetermined time period, a unit for detecting a reference point of each R wave of the QRS groups in the electrocardiographic wave stored in the memory unit, a unit for displaying the electrocardiographic wave stored in the memory unit, and a control unit for controlling the display unit so that a reference point of one of the QRS groups in the electrocardiographic wave is displayed at a predetermined position on displaying unit, the control unit being capable of shifting the QRS groups in a time scale while the electrocardiographic wave is displayed on the display unit.

Preferably, the apparatus further includes a measuring unit capable of sampling the electrocardiographic wave at a predetermined time period, and capable of converting the sampled electrocardiographic wave into a digital signal.

Further preferably, the first memory unit is adapted to store the digital signal converted by the measuring unit.

More preferably, the first memory unit consists of a plurality of first addresses and a first pointer, each of the plurality of first addresses being capable of storing the digital signal, the first pointer being adapted to be used for reading the digital signal stored in the first address and for writing the digital signal into any one of the plurality of first addresses.

The first pointer is adapted to be incremented until the plurality of first addresses being filled with a plurality of digital signals converted by the measuring unit, preferably.

The detecting unit is capable of calculating a difference of the digital signal stored in the first address, and capable of detecting a reference point of the QRS groups of the digital signal by determining a minimal value of the difference calculated thereby, preferably.

The apparatus further includes second memory unit capable of storing a value of any one of the first addresses in the first memory unit having a digital signal corresponding to the reference point detected by the detecting unit, preferably.

Preferably, the second memory unit consists of a plurality of second addresses and a second pointer, each of the plurality of second addresses being capable of having address data, the second pointer being used for reading the address data from any one of the plurality of second addresses and for writing the address data into any one of the plurality of second addresses.

More preferably, the control unit includes a time counter capable of counting an inactive period, and also capable of preventing the detecting unit from delivering a R wave until a predetermined time period being expired after delivering a preceded R wave.

Furthermore preferably, the time counter is so arranged that a value of the R wave is detected at a time when a value D is smaller than a valued $D_{th}$ while a value counted by the time counter is greater than a predetermined set value, the value D being a difference value calculated by the detecting unit corresponding to a value of one of the first addresses pointed by the first pointer in the first memory unit, and the value $D_{th}$ being a threshold value for calculating a reference point.

The detected value of the R wave is preferably stored in the second memory unit by storing the value of one of the first addresses in the first memory unit pointed by the first pointer therein into one of the second addresses of the second memory unit pointed by the second pointer therein.

The detecting unit is so arranged that the threshold value $D_{th}$ is set to be a minimal possible value of the difference value as an initial value, and the reference point indicating a position of the R wave is determined as a point at where the difference value becomes smaller than the threshold value $D_{th}$ while the difference value is successively read from the plurality of first addresses of the first memory unit, preferably.

The address data of one of the first addresses in the first memory unit corresponding to the reference point is preferably stored in one of the second addresses of the second memory unit pointed by the second pointer therein, and the threshold value $D_{th}$ is updated every period of N seconds by referring to the minimal value of the difference obtained within the period of N seconds until the first and second pointers and the time counter are updated, the N being any positive integer.

The control unit is capable of incrementing or decrementing the value of the second address indicated by the second pointer in the second memory, and a waveform displayed by the displaying unit is shifted to a left side or a right side by an amount corresponding to a predetermined number of the QRS groups, preferably.

Preferably, a value of one of the second addresses pointed by the second pointer in the second memory unit is equivalent to a value of one of the first addresses in the memory unit, the value in one of the first addresses being the converted digital signal corresponding to the reference point.

The control unit is capable of executing all processes in a time series manner, preferably.

Further preferably, the control unit is capable of executing all processes simultaneously in real time.

The advantages of the above-mentioned apparatus are the reference point of one QRS group among a plurality of QRS groups of the electrocardiographic signals is always displayed on a given position of the screen, and further, by a fixed operation, the right or the left section of the QRS group, which is a succeeding or preceding time, is accordingly shifted to be displayed. Therefore, it becomes easy to visualize the change between the QRS group on the above-described given position and the next QRS group, that is, the change of the R-R intervals. Furthermore, the display between the QRS group on the rightmost end of the screen and the QRS group on the leftmost end will not be interrupted.

Further objects and advantages of the present invention will be apparent from the following description, reference being had to the accompanying drawings wherein preferred embodiments of the present invention are clearly shown.

BRIEF DESCRIPTION OF THE DRAWINGS

FIG. 11 is a flow chart showing the operation performed by the reference point detecting unit shown in FIG. 1;

DESCRIPTION OF THE PREFERRED EMBODIMENT

Figure 1:
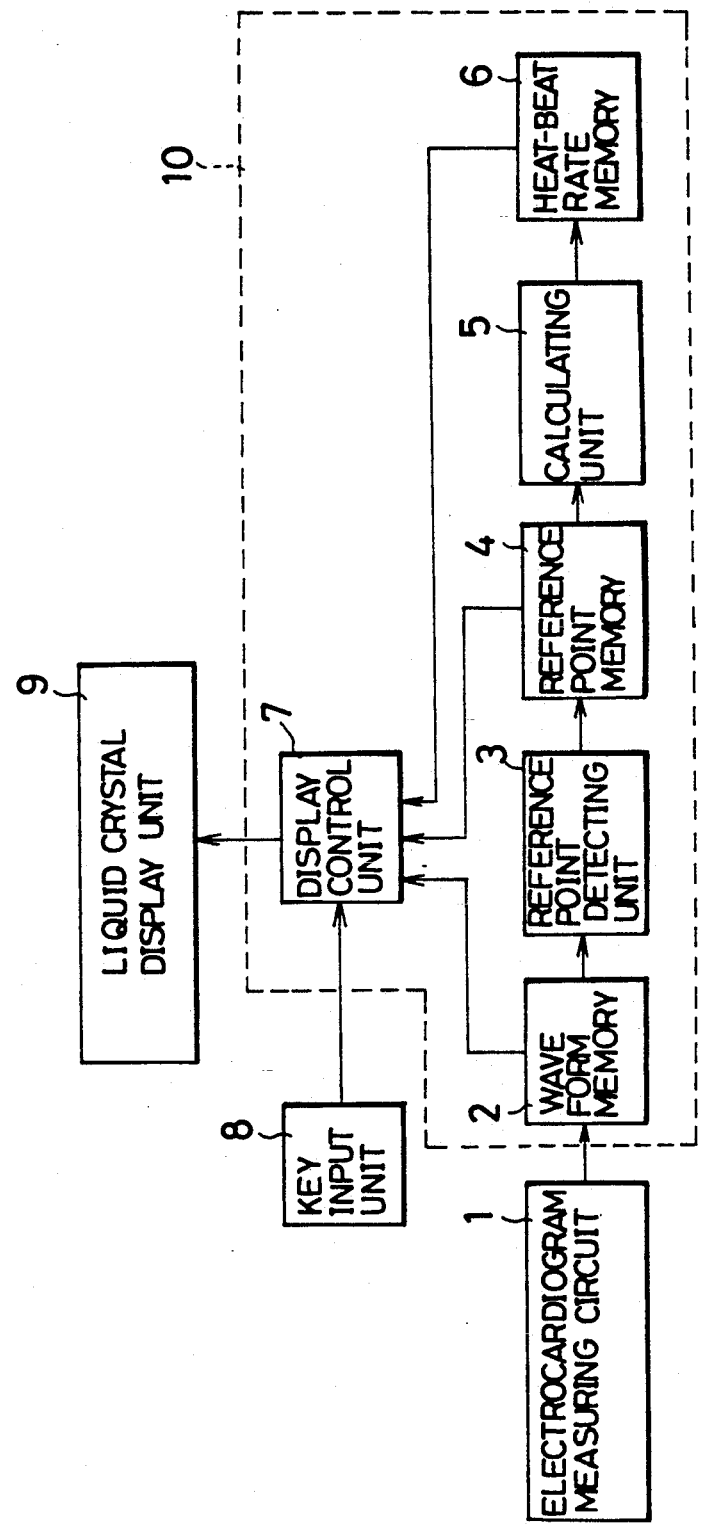
FIG. 1 shows a block diagram illustrating of an embodiment the electrocardiogram recording apparatus according to the present invention.

An embodiment of the present invention will now be described in detail with reference to the accompanying drawings FIG. 1 is a block diagram showing the main components of the electrocardiogram recording apparatus of an embodiment according to the present invention.

As shown in FIG. 1, numeral 1 indicates an electrocardiogram measuring circuit for measuring electrocardiograph signals, for converting the electrocardiograph signals into digital data, and for outputting digital data. Numeral 2 indicates a waveform memory for storing the electrocardiographic wave data of the digital data outputted from the electrocardiogram measuring circuit 1 for a fixed time, for example, ten minutes. Numeral 3 denotes a reference point detecting unit for detecting negative maximum points exceeding the fixed threshold values to set the detected negative maximum points to reference points in QRS groups by differentiating the electrocardiographic wave data outputted from the waveform memory as will be described later. Numeral 4 indicates a reference point memory for storing the detected reference points outputted from the reference point detecting unit 3, while numeral 5 indicates a calculating unit for calculating instantaneous heart-beat rates by using the inverse number of the time difference between the adjacent reference points. Numeral 6 denotes a heart-beat rate memory for storing the instantaneous heart-beat rate calculated by the calculating unit. Numeral 7 indicates a display control unit for controlling the display of the electrocardiographic wave data after reading out from the waveform memory 2 in response to the key operation of a key input unit 8. Numeral 9 denotes a liquid crystal display unit used as display unit for displaying the electrocardiographic waveforms on the display screen.

In the above-described construction, a microcomputer 10 includes basically the waveform memory 2, the reference point detecting unit 3, the reference point memory 4, the calculating unit 5 for instantaneously calculating heart-beat rate, the heart-beat rate memory 6 and the display control unit 7.

The electrocardiogram recording apparatus according to this embodiment is constructed in the following way so as to easily visualize a change in the R-R intervals.

Figure 2:
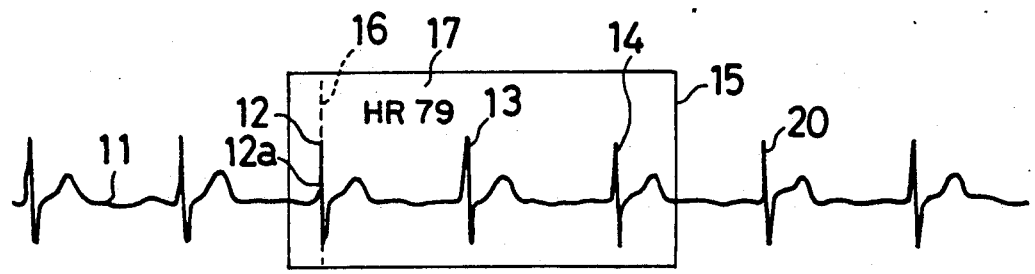
FIG. 2 shows an electrocardiogram and one example of the display screen in accordance with the electrocardiogram recording apparatus shown in FIG. 1.

FIG. 2 is a chart showing an electrocardiogram and one example of the display screen in accordance with this invention.

Figure 3A:
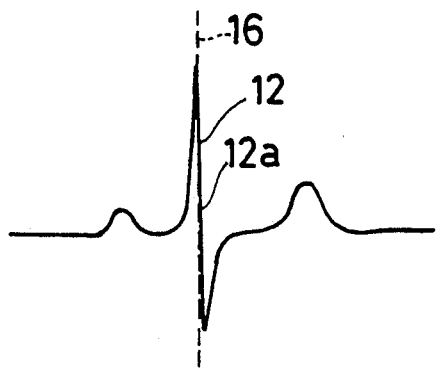
FIG. 3a and FIG. 3b show waveforms for explaining a detection of the reference point according to the electrocardiogram recording apparatus of FIG. 1.
Figure 3B:
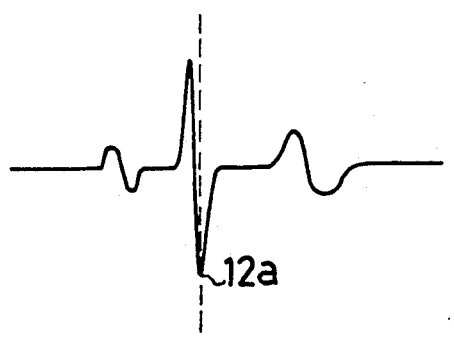

As shown in FIG. 2, three QRS groups 12 to 14 of a continuous electrocardiogram 11 are displayed on a rectangular screen 15. The reference point 12a of the QRS group 12, which is the leftmost among the three QRS groups 12 to 14, is indicated by a broken line 16 Positioned at a fixed place on the screen 15. This reference point 12a is a point detected by the reference point detecting unit 3. The reference point 12a is a negative maximum point which exceeds the fixed threshold value of the waveform shown in FIG. 3b. The waveform shown in FIG. 3b is a waveform differentiated by the QRS group 12 of the electrocardiogram waveform shown in FIG. 3a. In other words, the reference point 12a is a sharp point of the change in the electrocardiogram. The reference point detecting unit 3 detects each reference point for each QRS group of the electrocardiogram and stores each reference point in the reference point memory 4.

Figure 4:
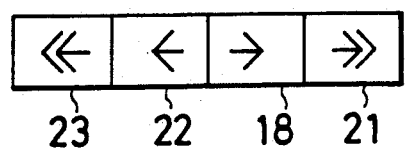
FIG 4 illustrates the operation keys of the electrocardiogram recording apparatus shown in FIG. 1.
Figure 5:
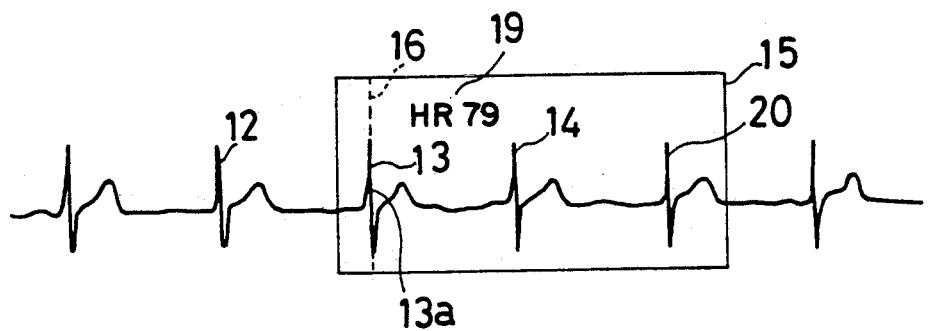
FIG. 5 shows an electrocardiogram and the display screen when the display screen of the electrocardiogram shown in FIG. 2 is shifted rightward.

An instantaneous heart-beat rate 17 between the QRS group 12 and the succeeding QRS group 13 is also displayed on the screen 15. Under this display condition, pressing of a one-heart-beat rate stroke key 18 (shown in FIG. 4) of the key input section 8 makes one of the QRS groups shift leftward, that is, pressing the one-heartbeat rate stroke key 18 makes one of the QRS groups shift leftward a distance proportional to the size of one group QRS of the electrocardiogram. As shown in FIG. 5, the reference point 13a of the QRS group 13 is then displayed at the fixed position 16 on the screen 15 as well as an instantaneous heart-beat rate 19 between the QRS group 13 and the succeeding QRS group 14 is also displayed, and a succeeding new QRS group 20 is displayed on the screen 15.

Figure 6:
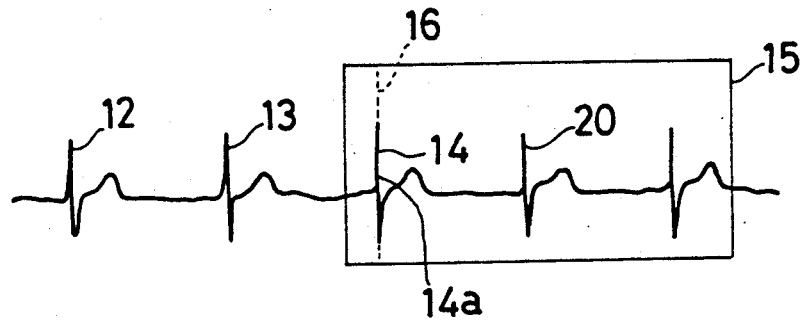
FIG. 6 shows the electrocardiogram and the display screen when the display screen shown in FIG. 5 is further shifted rightward.

Furthermore, under the display condition as shown in FIG. 2, pressing of a screen scroll key 21 (shown in FIG. 4) of the key input section 8, the electrocardiogram is shifted leftward only in a distance proportional to the size of two QRS groups only, as shown in FIG. 6. The reference point 14a of the QRS group 14 at the right end of the screen 15 is then displayed at the fixed position 16 on the screen 15.

Pressing of a one heart-beat rate stroke key 22 or a screen scroll key 23 (shown in FIG. 4) of the key input section 8, the electrocardiogram is shifted in a reversed direction of the above mentioned direction, that is, the electrocardiogram is shifted rightward. Further, when the keys 18, 21, 22 and 23 of the input section 8 are pressed in succession, the screen 15 keeps scrolling with the QRS groups displayed at a rate of three QRS groups per second.

As described above, when all three QRS groups have been displayed on the screen 15 after the electrocardiogram from the waveform memory 2 has been read, accordingly the display control unit 7 displays the reference point of the QRS group which is the leftmost among the three QRS groups at the fixed position 16 on the screen 15 based on the reference point data from the reference point memory 4. The display control unit 7 also shifts the QRS groups rightward or leftward only in a distance proportional to the size of one or two QRS groups in order to display the QRS groups in response to a key operation of the four keys 18, 21, 22 and 23.

The reference point, displayed on the screen of the liquid crystal display 9, of the QRS group which is the leftmost among the three QRS groups of the electrocardiogram is always displayed accordingly at the predetermined position 16 on the screen 15, and the reference point is shifted either rightward or leftward by a predetermined operation for only predetermined numbers of QRS groups. For the above reasons, it becomes easy to visualize the changes of the intervals between the QRS group at the predetermined position and the succeeding QRS groups, that is, the changes in the R-R intervals. In addition, there is no interruption between the display of the rightmost QRS group and the leftmost QRS group which is to be displayed next.

Moreover, since an instantaneous heart-beat rate is also displayed, it is possible to determine a change in the R-R intervals more accurately in this embodiment.

Although the three QRS groups are displayed on the screen 15 in this embodiment, the number of the QRS groups is not limited to three in the present invention. The reference point of the QRS group is not limited to a negative maximum point of the differential waveform, but a R wave, which is a peak wave of the QRS group, may also be utilized.

In the following, the operation of the apparatus for recording an electrocardiogram, when the processes in the waveform memory 2, reference point detecting unit 3 and the reference point memory 4 in FIG. 1 are performed in a time-series manner, will be described as an example.

Figure 7:
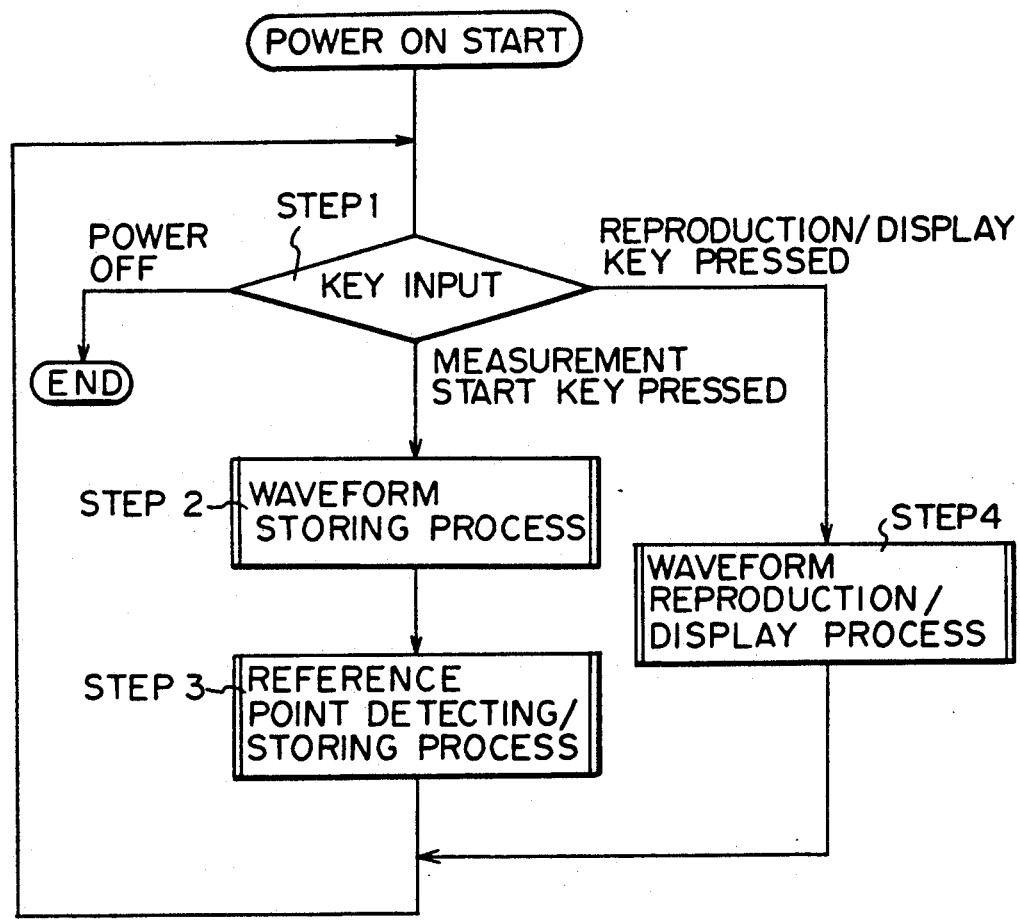
FIG. 7 shows the flow of the operation process of the apparatus in FIG. 1.

FIG. 7 shows the flow of the above-mentioned operation process. When the power of the apparatus for recording the electrocardiogram is turned on, the process proceeds to STEP 1 and the process waits for an entry through a key in the key input unit 8. When a measurement start key (not shown) is pressed, the process proceeds to STEP 2 and the waveform is stored. In a subsequent STEP 3, a detection of the reference point and a storage operation are performed so as to record the cardiogram. After the recording, the process returns to STEP 1 to wait for the next key input. When the reproduction display key (not shown) is pressed in STEP 1, the process proceeds to STEP 4 in which the waveform is reproduced and displayed, and a cardiographic waveform as shown in FIG. 2 is displayed on a liquid crystal display unit 9 in accordance with an input from the key input unit 8. When a display finish instruction is input through a key in the waveform reproduction display routine performed in STEP 4, the process returns to STEP 1 to wait for a next key input. If an instruction is given through a power-off key (not shown) of the key input unit 8, the power is turned off and the process is terminated.

The above-mentioned waveform storage processing routine performed in STEP 2 of the flow show in FIG. 7 will be described in details.

Electrocardiographic data are sampled at a predetermined sampling period by the electrocardiogram measuring circuit 1 and are A/D-converted into digital signals. The digital electrocardiographic data are successively stored in the waveform memory 2.

Figure 8:
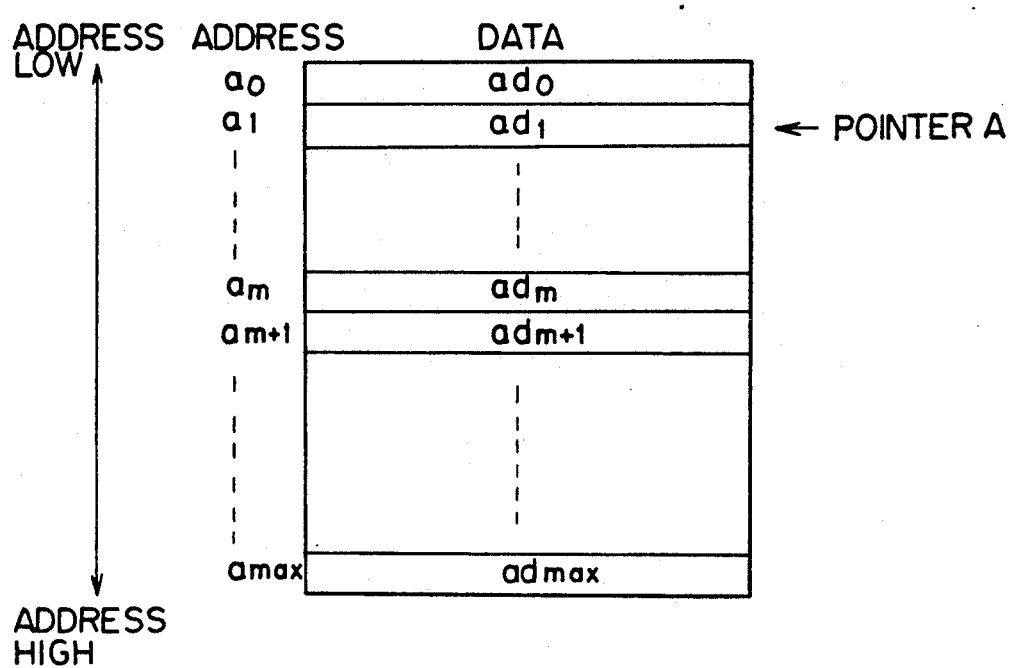
FIG. 8 shows the construction of the waveform memory shown in FIG. 1.

FIG. 8 shows the memory construction of the waveform memory 2. In this figure, symbols $a_0, a_1, \ldots, a_{max}$ represent the address in the waveform memory 2, $ad_0$, $ad_1, \ldots, ad_{max}$ represent A/D converted data stored in the waveform memory 2 at the respective addresses, and pointer A indicates a memory address pointer used in reading and writing data.

Figure 9:
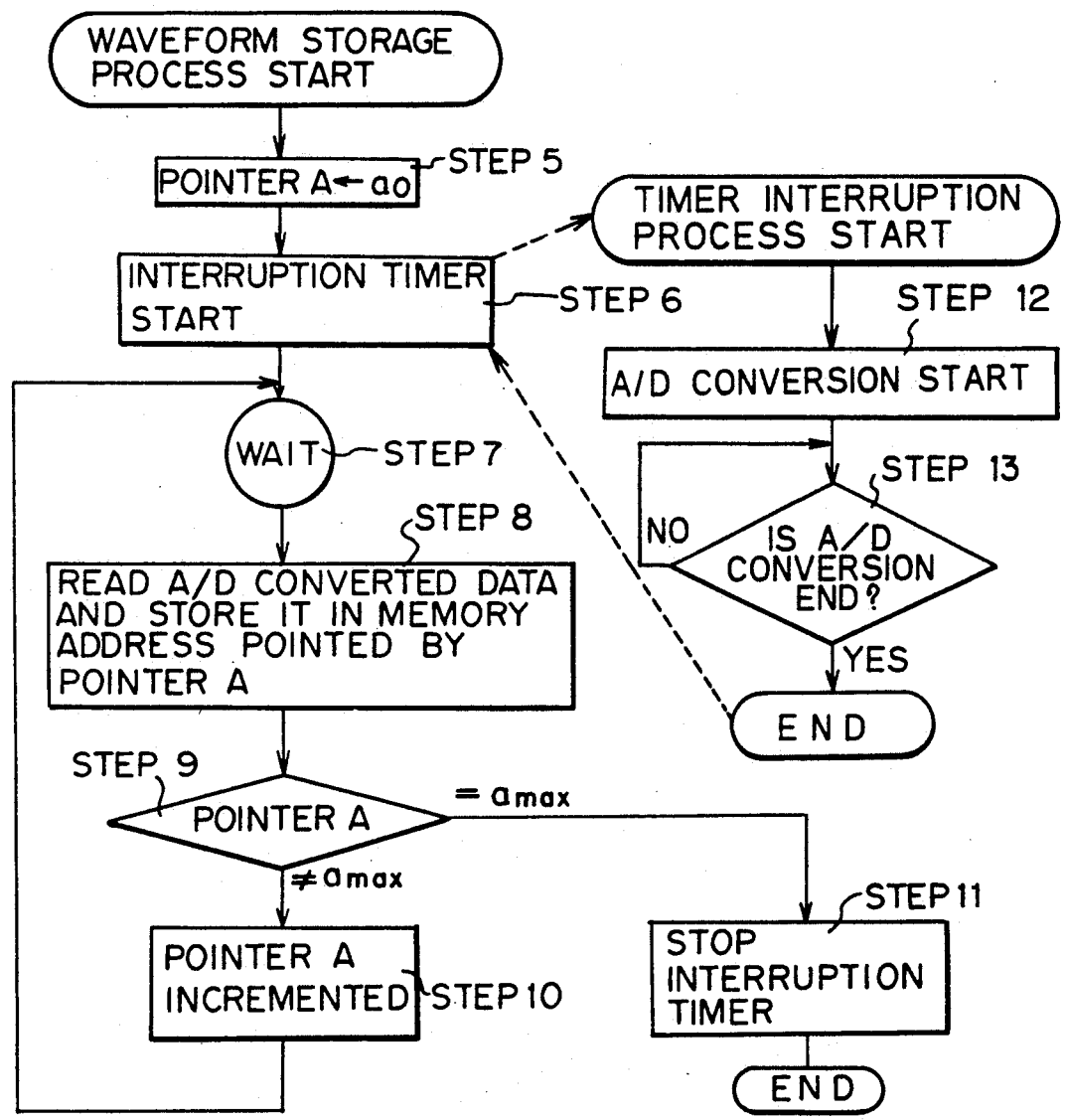
FIG. 9 is a flow chart showing the waveform storing process performed by the waveform memory.

FIG. 9 is a flow chart showing the waveform storing process performed by the waveform memory 2.

As the waveform storage process is started, the pointer A is initialized in STEP 5 so as to point a leading-end address of the waveform memory 2 shown in FIG. 8. Then, in STEP 6, an interruption timer (not shown) is started so as to cause an interruption at a sampling period $f_{samp}$. The process then proceeds to STEP 7 to wait for an interruption ruled by the interruption timer. When a timer interruption has taken place, a timer interruption routine is started in which A/D conversion is started in STEP 12. When the completion of A/D conversion is confirmed in STEP 13 the timer interruption routine is terminated. The process then returns to STEP 8. In STEP 8 the waveform memory 2 reads the result of the A/D conversion and stores the read value at the address appointed by the pointer A. In STEP 9, a completion of the waveform storage is determined on the basis of the value of the pointer A. If the pointer has pointed the final address, the control is proceeds to STEP 11 in which the waveform storage operation is terminated. Otherwise, the process proceeds to STEP 10 and the value of the pointer A is changed to the value of the address in which the next A/D converted data is to be stored. Then, the process returns to STEP 7 to wait for a generation of the interruption so as to continue the waveform storage operation.

Thus, the electrocardiographic data which is A/D converted for the first time by the electrocardiographic measuring circuit 1 is stored at the address pointed by the pointer A and the content of the pointer A is incremented to point the address $a_1$. The second A/D converted electrocardiographic data obtained after an elapse of a predetermined time determined by the sampling period $f_{samp}$ is stored at the address $a_1$ and the content of the pointer A is incremented to $a_2$. Thus, in general, the m-th A/D converted electrocardiographic data is stored at the address $a_m$ and the content of the pointer A is incremented to $a_{m+1}$. Then, the described operation is repeated at a predetermined time interval until the waveform memory is completely filled with the electrocardiographic data and then the waveform storage operation is terminated.

Next, the reference point detection and the storage operation performed in STEP 3 of FIG. 7 will be described. The reference point detecting unit 3 calculates the difference (differentiation) of the electrocardiographic data stored in the waveform memory 2 and detects the reference point of the QRS groups by determining the minimum value of the difference. Then, the addresses of the waveform memory 2 in which the A/D converted values of the waveforms corresponding to the reference points are determined, and the values of these addresses are stored in the reference point memory 4.

Figure 10:
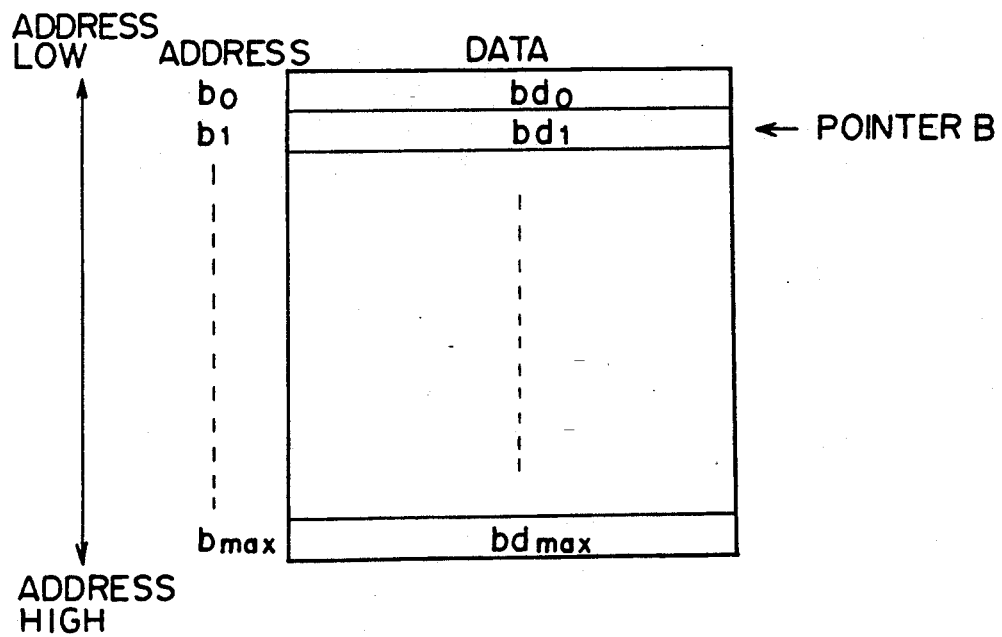
FIG. 10 shows the construction of the reference point memory shown in FIG. 1.

FIG. 10 shows the memory construction of the reference point memory 4. In FIG. 10, a pointer B indicates the memory address pointer which is used for reading and writing the address data $bd_0, bd_1, \ldots, bd_{max}$ concerning the reference points in addresses $b_0, b_1, \ldots, b_{max}$.

FIG. 11 is a flow chart showing the operation performed by the reference point detecting unit 3. As detecting and storing process of the reference point is started, an initialization of a variable is performed in STEP 14. In this operation, the pointer A is used for reading data from the waveform memory 2 shown in FIG. 8, and the pointer A is initialized so as to point the address $a_1$. On the other hand, the pointer B is used for writing the detected reference point data in the reference point memory 4 shown in FIG. 10, and the pointer B is initialized so as to point an address $b_0$. $D_{min}$ represents a variable for storing the minimum value of the difference of the A/D data, and the variable $D_{min}$ has the "maximum possible value of the difference value" as its initial value. $D_{th}$ represents a threshold value for detecting the reference point, and the variable $D_{th}$ has the "minimum possible value of the difference value" as its initial value. An refractory period time counter $TC_r$ is initialized to zero. The inactive period time counter $TR_c$ operates to prevent the reference point detecting unit 3 from delivering a R wave until a predetermined time is passed after the delivery of the preceding R wave.

In STEP 15, the time counter $TC_{th}$ indicative of a time interval determining the minimum value detection threshold used in the detection of the reference point is set to a value corresponding to N seconds. In STEP 16, the difference value at the address pointed by the pointer A is calculated and is stored in the variable D. In STEP 17, the above-mentioned variable D is compared with the variable $D_{min}$ in order to determine the minimum value of the difference, so that the minimum value is stored in the variable $D_{min}$. In STEP 18, an operation is performed for detecting the reference point. It is judged that a value of a R wave has been detected at a time when the difference value D is smaller than the threshold value $D_{th}$ while the content of the refractory period time counter $TC_r$ is greater than the set value $N_2$. Then, the process proceeds to STEP 19 in which the detected value of R wave is stored in the reference point memory 4 shown in FIG. 1 (i.e., in the reference point memory 4 shown in FIG. 10). The storage of the detected value is performed by storing the value in the waveform memory 2 pointed by the pointer A into the address of the reference point memory 4 pointed by the pointer B. At the same time, the refractory period time counter $TC_r$ is cleared. STEP 20 determines a completion of the operation for detecting and storing the reference point. The process is terminated when either one of the pointers A or B points the final address of the memory. The pointers and the counters are updated in STEPs 21 to 23. In STEP 24, an updating and a judgment of the threshold value $D_{th}$ are performed and, in STEP 25, the threshold value $D_{th}$ is updated once per N seconds.

In the reference point detecting and storing operation, the threshold value $D_{th}$ is set to the "minimum possible value of the difference value" as the initial value. Therefore, the difference value of the data cannot be smaller than the threshold value $D_{th}$ within the period of N seconds after the start, i.e., until the content of the counter $TC_{th}$ is reduced to zero for the first time. The data obtained within such a period is used only for updating the threshold value $D_{th}$. Then, the data are successively read from the waveform memory 2, and the point at which the difference value has become smaller than the threshold value $D_{th}$ is determined as the reference point, i.e., the position of the R wave. It is to be noted, however, that a monitoring is performed by the refractory period timer $TC_r$ so that the time interval between one R wave and the next R wave does not become shorter than the refractory period. The address data of the address corresponding to this reference point (i.e., the value indicated by the pointer A) is stored in the address of the reference point memory 4 which is pointed by the pointer B. The threshold value $D_{th}$ is updated every N seconds by making reference to the minimum value of the difference obtained within this period of N seconds. This operation is repeated while the memory pointers and the timer counters are updated.

A description will now be given to the operation for reproducing and displaying waveform performed in STEP 4 of the flow shown in FIG. 7.

Figure 12:
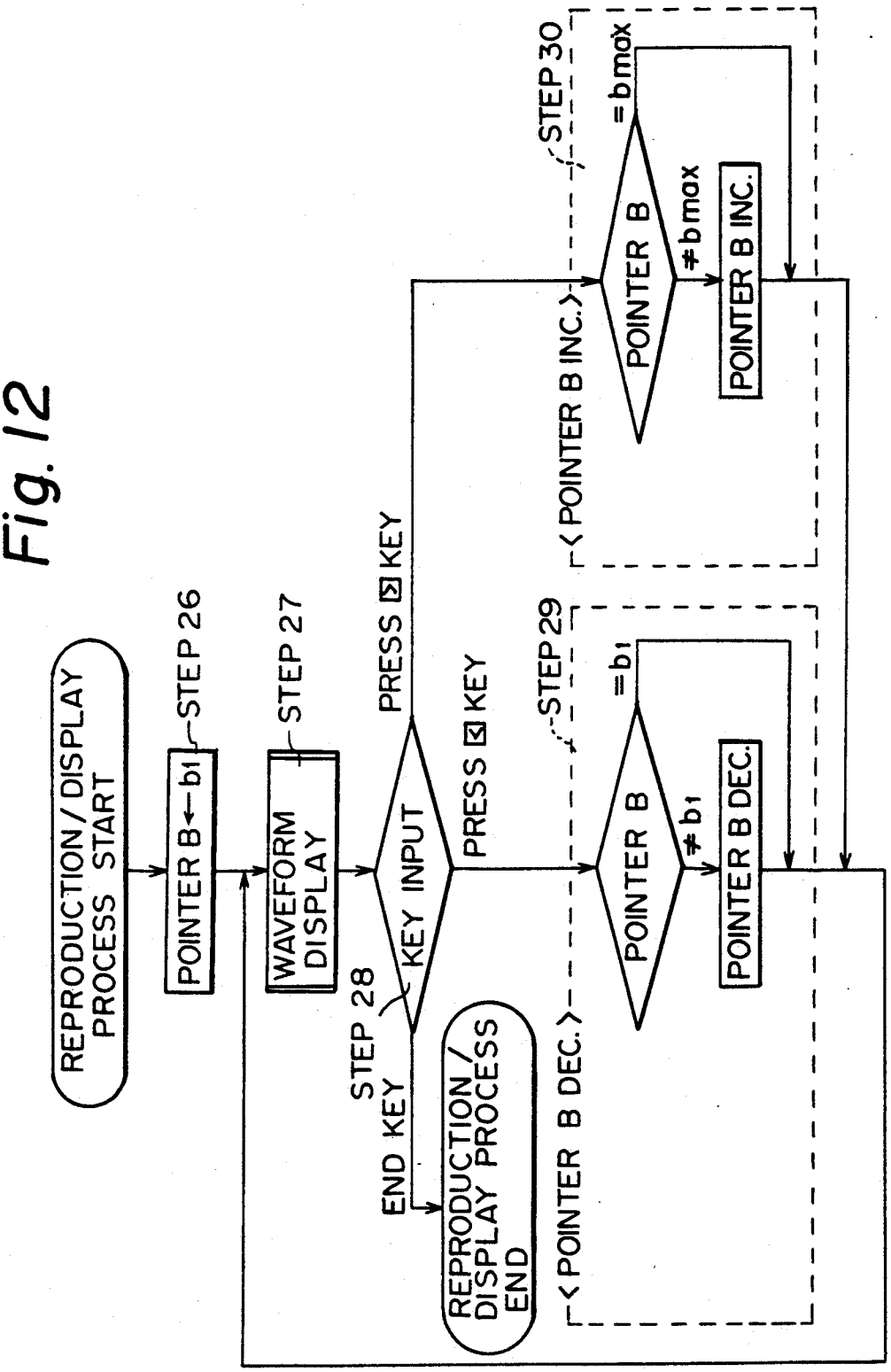
FIG. 12 is a flow chart of the operation for reproducing and displaying the waveform performed by the display control unit shown in FIG. 1.

FIG. 12 is a flow chart of the operation for reproducing and displaying the waveform performed by the display control unit 7 shown in FIG. 1.

As the reproducing display process is started, the pointer B for reading the reference point address from the reference point memory 4 is initialized to $b_1$ which is the second reference point address. The reason for not using the first reference point address $b_0$ as the initial value of the pointer B is that the waveform containing the reference point recorded for the first time may lack the portion earlier that the reference point, e.g., the P wave.

In STEP 27, the waveform containing the reference point pointed by the pointer B is displayed so as to be located on the left end of the display frame. The detail of this operation will be described later.

In STEP 28, an operation of the inputting the next key after the display of one frame of the electrocardiographic waveform is waited. As the key is Pressed in this state, the process proceeds to STEP 29 or STEP 30 so as to increment or decrement the address value indicated by the pointer B and the waveform displayed in STEP 27 is shifted to the left or right by amount corresponding to a predetermined number of groups of QRS waves.

Figure 13:
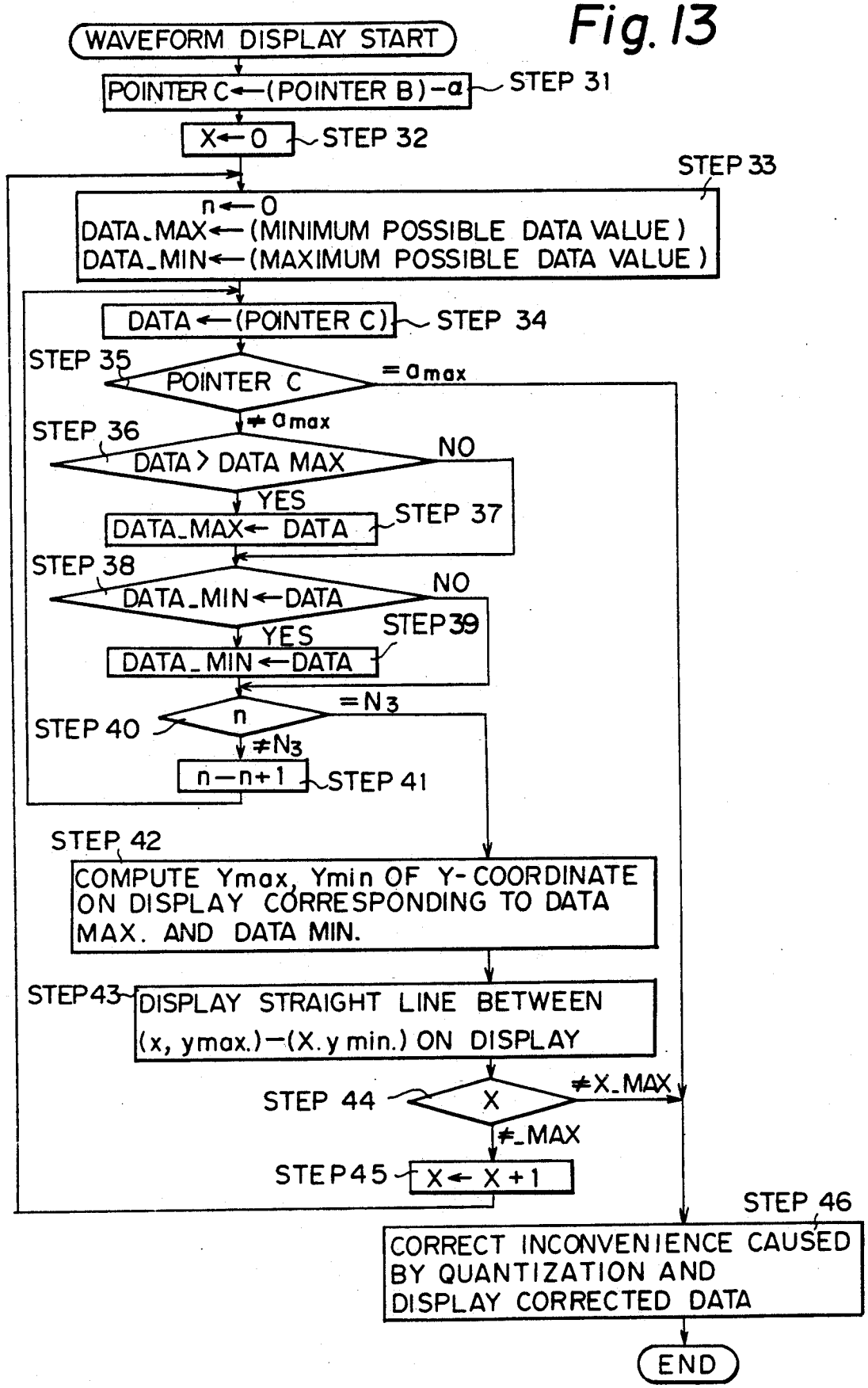
FIG. 13 shows the detail of the routine performed in a step for displaying the waveform.
Figure 14:
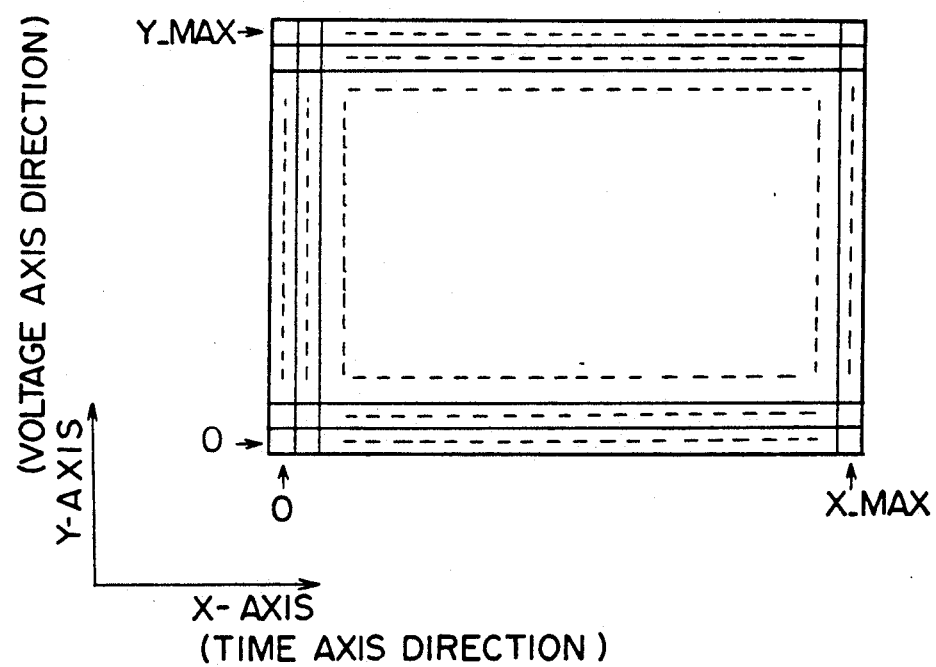
FIG. 14 shows the structure of the display frame of the liquid crystal display unit shown in FIG. 1.

FIG. 13 shows the detail of the routine performed in STEP 27 for displaying the waveform, while FIG. 14 shows the structure of the display frame of the liquid crystal display unit 9 shown in FIG. 1.

As the waveform display function is started, in STEP 31, the display control unit 7 reads the content of the reference point memory 4 at the address pointed by the pointer B, i.e., the address in the waveform memory 2 where the A/D converted electrocardiographic data at the reference point is stored. Then, in order to calculate the reference point on the display (waveform position at a moment which is earlier than the reference point by a predetermined time, almost immediately before the P wave), a value obtained by subtracting a predetermined value α from the value in the address is stored in the address pointed by a pointer C which is used for reading data from the waveform memory 2 during displaying.

In STEP 32, the variable X indicative of the X-axis coordinate position of the display is initialized to zero. In STEPs 33 to 41, the contents of the waveform memory 2 are successively read to obtain pieces of data of a number which correspond to the X-axis display resolution of address offered by the pointer C. The maximum and minimum values of the thus read data are respectively stored in the variables DATA MAX and DATA MIN. Then, in STEPs 42 and 43, Y-axis coordinate values on the display corresponding to the maximum and minimum values of the read data are calculated. The two points thus determined are connected by a straight line on the liquid crystal display unit 9 in FIG. 1. In STEP 44, a completion of the waveform display processing is determined on the basis of the X-coordinate value of the data on the display. If the X-coordinate value has not reached yet the dot line which is on the right end of the display frame, the process returns to STEP 45 in which the X-axis coordinate value is incremented. The process then returns to STEP 33 to continue the waveform display process. If the right end dot line has been reached by the X-axis coordinate value, the process proceeds to STEP 46 in which any inconvenience caused by quantization is corrected in order to correct the display on the liquid crystal display unit 9.

In the illustrated operation, the processes of the respective parts are executed in a time-series manner. This, however, is not exclusive and the operations for the storage of the waveform, the detection and the recording of reference point, the reproduction and the display may be performed simultaneously in real time.

Many widely different embodiments of the present invention may be constructed without departing from the spirit and scope of the present invention. It should be understood that the present invention is not limited to the specific embodiments described in this specification, except as defined in the appended claims.

What is claimed is:

1. An apparatus for recording electrocardiographic signals capable of displaying a change of spike intervals of adjacent QRS groups among a plurality of QRS groups of an electrocardiographic wave, said apparatus capable of displaying a time change of an electric potential with heart pulsations, said QRS groups showing an electric potential at a start of a ventricular systole, said apparatus comprising:

means for measuring an electrocardiographic wave comprised of a plurality of QRS groups;

a first memory means having a plurality of addresses for storing said electrocardiographic wave measured by said measuring means;

means for detecting said QRS groups in said electrocardiographic wave stored in said first memory means;

means for detecting a reference point of each R wave of said QRS groups;

means for displaying a plurality of adjacent QRS groups of said electrocardiographic wave stored in said first memory means; and a control means for controlling said display means so that said plurality of adjacent QRS groups of said electrocardiographic wave are displayed on said display means with a reference point of any one of said QRS groups in said electrocardiographic wave fixed at a predetermined position on said display means, said measuring means including means for sampling said electrocardiographic wave and means for converting said sampled electrocardiographic wave into a series of digital signals, said detecting means including means for subtracting each of said digital signals from a preceding digital signal in said series of digital signals to obtain a difference for each digital signal and means for detecting a reference point of said QRS groups by identifying a digital signal having a minimum value of said difference calculated thereby.

2. An apparatus according to claim 1, and further including means for storing said electrocardiographic wave by storing said series of digital signals formed by converting said sampled electrocardiographic wave.

3. An apparatus according to claim 1, wherein said apparatus further comprises a second memory means having a plurality of addresses and at least one pointer for storing information located in an address of said first memory means corresponding to said reference point detected by said detecting means.

4. An apparatus according to claim 3, wherein said control means includes means for incrementing or decrementing said at least one pointer in said second memory means so that a waveform displayed by said displaying means is shifted to a left side or a right side by an amount corresponding to a predetermined number of said QRS groups.

5. An apparatus according to claim 1, wherein said control means includes a time counter for counting an inactive time period of said apparatus, and said detecting means includes means responsive to said time counter to prevent detection of a reference point until a predetermined time period counted by said time counter expires after detecting a preceding reference point.

6. An apparatus according to claim 5, wherein said detecting means includes means for calculating difference values D by subtracting a digital signal from a preceding digital signal in said series of digital signals and means for detecting a reference point at a time when a value D is less than a threshold value Dth while a time value counted by said timer counter is greater than a predetermined time period.

7. An apparatus according to claim 6, further comprising a second memory means having a plurality of addresses for storing a value of an address of said first memory means corresponding to a reference point detected by said detecting means.

8. An apparatus according to claim 7, wherein said detecting means includes means to set said threshold value $D_{th}$ to a minimum possible value of said difference value as an initial value, and wherein said detecting means records successive digital signals from said first memory means so as to detect a reference point where said difference value becomes less than said threshold value $D_{th}$.

9. An apparatus according to claim 8, wherein said electrocardiographic wave has periods of N seconds, where N is any positive integer, said detecting means further includes means for determining a minimum value of said difference value D obtained within every period of N seconds, and means for updating said threshold value $D_{th}$ with reference to said minimum value every period.

10. An apparatus according to claim 1, wherein said control means includes means for controlling the display of said adjacent QRS groups in a time sequential manner.

11. An apparatus according to claim 1, wherein said control means includes means for controlling the display of said adjacent QRS groups simultaneously in real time.

* * * * *